US012806350B2

(12) United States Patent
Fang

(10) Patent No.: US 12,806,350 B2
(45) Date of Patent: Nov. 24, 2026

(54) RELIABLE COMPACT INHALATION DEVICE FOR ASTHMA AND CHRONIC OBSTRUCTIVE PULMONARY DISEASE

(71) Applicant: Win Htay Fang, Fremont, CA (US)

(72) Inventor: Win Htay Fang, Fremont, CA (US)

( * ) Notice: Subject to any disclaimer, the term of this patent is extended or adjusted under 35 U.S.C. 154(b) by 885 days.

(21) Appl. No.: 18/111,648

(22) Filed: Feb. 20, 2023

(65) Prior Publication Data

US 2024/0277950 A1 Aug. 22, 2024

(51) Int. Cl.
*A61M 15/06* (2006.01)
*A61M 15/00* (2006.01)

(52) U.S. Cl.
CPC ........ *A61M 15/06* (2013.01); *A61M 15/0006* (2014.02); *A61M 15/0028* (2013.01); *A61M 15/0045* (2013.01); *A61M 15/0071* (2014.02); *A61M 15/0015* (2014.02); *A61M 15/0016* (2014.02); *A61M 2202/064* (2013.01)

(58) Field of Classification Search
CPC .............. A61M 15/06; A61M 15/0006; A61M 15/0071; A61M 2202/064; A61M 15/0045; A61M 15/0015; A61M 15/0016; A61M 15/0028; A61M 11/04; A61M 15/00–0085; A24F 42/00–60
See application file for complete search history.

(56) References Cited

U.S. PATENT DOCUMENTS 844,097 A * 2/1907 Caldwell ............... A61M 15/08 128/203.22
2,503,732 A * 4/1950 Heisterkamp ..... A61M 15/0015 128/203.15

(Continued)

FOREIGN PATENT DOCUMENTS

CN 101522063 A * 9/2009 ............. A24F 42/60
FR 2654002 A1 * 5/1991 ............. A24F 42/60
TW 201332461 A * 8/2013

OTHER PUBLICATIONS

English translation for TW 201332461, machine translated by espacenet.com.*

(Continued)

*Primary Examiner* — Tu A Vo

(57) ABSTRACT

The invention provides a compact inhalation device (CID) to effectively deliver inhalation medication to a patient. The CID includes a mouth piece, a drug chamber and an air flow chamber, wherein the mouth piece, the drug chamber and the air flow chamber are connected to form a cylinder-shaped device, which is similar to a cigarette, and provide at least medication contained in the drug chamber to the patient via the mouth piece. One end of the mouth piece fits a patient's mouth. The other end of the mouth piece is connected to a first end of the drug chamber, and a second end of the drug chamber is connected to a first end of the air flow chamber, wherein the connections between them use a twisted close/open mechanism or a flapped flow close/open mechanism. A second end of the air flow chamber has an opening for ambient air flow. The CID is a cigarette shaped device to use, convenient and even available to use in public places without being noticed by surrounding with compliance rate increased and medication reached to most peripheral parts of the lung more effectively.

12 Claims, 5 Drawing Sheets

(56) References Cited

U.S. PATENT DOCUMENTS

| | | | | | |
|---|---|---|---|---|---|
| 2,642,063 | A * | 6/1953 | Brown | A61M 15/0028 | |
| | | | | 128/203.15 | |
| 4,694,824 | A * | 9/1987 | Ruderian | A61M 16/108 | |
| | | | | 128/203.22 | |
| 9,795,751 | B2 | 10/2017 | Bilgic | | |
| 2004/0094146 | A1 * | 5/2004 | Schiewe | B05B 11/02 | |
| | | | | 128/200.14 | |
| 2005/0155601 | A1 * | 7/2005 | Steiner | A61M 15/0051 | |
| | | | | 128/200.23 | |
| 2007/0045288 | A1 * | 3/2007 | Nelson | A61M 11/041 | |
| | | | | 219/533 | |
| 2013/0312777 | A1 * | 11/2013 | Burghardt | A61M 15/0043 | |
| | | | | 131/329 | |
| 2016/0007649 | A1 * | 1/2016 | Sampson | A24F 7/04 | |
| | | | | 131/187 | |
| 2016/0270441 | A1 * | 9/2016 | Lewis | A24F 40/42 | |
| 2017/0216538 | A1 * | 8/2017 | Kinsey | A61M 15/0021 | |
| 2019/0098930 | A1 * | 4/2019 | Fallon | A61M 15/06 | |
| 2019/0110517 | A1 * | 4/2019 | Rogers | A24F 1/00 | |
| 2019/0254345 | A1 * | 8/2019 | Hepworth | A61M 11/042 | |
| 2020/0113234 | A1 * | 4/2020 | Patoret | A61M 15/0003 | |
| 2024/0108060 | A1 * | 4/2024 | Pauls | A61M 15/002 | |

OTHER PUBLICATIONS

English translation for FR 2654002, machine translated by espacenet.com.*

* cited by examiner

Mouth piece fit to twist on drug chamber 301

Untwist/Normal Position 302

Closed Drug Chamber

Twisted Position 303

Opened Drug Chamber

Normal Position 401

- All Valve Closed

In Use Position 402

AB - Drug Chamber Open Valve (Drug flow to Mouth)
BC - Air Flow Chamber Open Valve (Air Flow)

Enlarged view of medication chamber to insert into a cigarette shaped inhaler

RELIABLE COMPACT INHALATION DEVICE FOR ASTHMA AND CHRONIC OBSTRUCTIVE PULMONARY DISEASE

The present invention relates to a compact design for a device used with inhaled medicines and, more specifically, a reliable compact design for a dry power inhaler (DPI).

BACKGROUND

It has been a very potent and effective medication (powder form) to treat Asthma and Chronic Obstructive Pulmonary Disease (COPD). However, currently available delivery devices are not effectively spread medication to most peripheral part of the airway system in the lung, where medication effects are needed. Moreover, these devices are ugly, making patients uncomfortable to use, and mouthpieces are generally not a perfect fit to inhale all amounts of medication to deliver to the intended part of the lung.

Therefore, a need exists to develop a system and method to effectively deliver inhalation medication to a patient of needed. A cigarette shaped device may be easy to use, convenient and even available to use in public places without being noticed by the surrounding with compliance rate increased and medication reached to most peripheral parts of the lung more effectively are desired. The device may provide not only a mouthpiece perfect fit for every user, in using medication mimic smoking, but also a patient can use medication in public compliance rate higher. Effectively sucking, even repeatedly until all single powder medication is inhaled and more precise delivery of medication can be achieved.

A design as a cigarette may also stimulate suction and lips easily adapt mouthpiece of cigarette and instantly synchronize suction of powder medication, if one puff is not enough to empty all medication, a patient can repeat several puff until last powder of medication sucked in and more effective delivery results in style.

SUMMARY OF THE INVENTION

The following presents descriptions of one or more embodiments in order to provide a basic understanding of such embodiments. This summary is not an extensive overview of all contemplated embodiments and is intended to neither identify key or critical elements of all embodiments, nor delineate the scope of any or all embodiments. Embodiments of the present invention address the above needs and/or achieve other advantages by providing a reliable compact design for a dry power inhaler (DPI).

Specifically, the present invention provides a compact inhalation device (CID). The CID comprises a mouth piece, a drug chamber and an air flow chamber. The mouth piece, the drug chamber and the air flow chamber are connected to form a cylinder-shaped device, which is similar to a cigarette. For the purpose of the invention, the mouth piece, the drug chamber and the air flow chamber are coupled to provide at least medication contained in the drug chamber to a patient via the mouth piece;

In one embodiment, one end of the mouth piece fits a patient's mouth and other end of the mouth piece is connected to a first end of the drug chamber using a twisted close/open mechanism or a flapped flow close/open mechanism. Similarly, a second end of the drug chamber is connected to the one end of the air flow chamber using the twisted close/open mechanism or the flapped flow close/ open mechanism; and other end of the air flow chamber has an opening for flow with ambient air.

The twisted close/open mechanism includes two surfaces with at least one opening on each surface, and the process of aligning the at least one opening by twisting provides an open flow condition and unaligned to block the at least one opening by twisting provides a close flow condition.

Difference from the twisted close/open mechanism, the flapped flow close/open mechanism includes two surfaces with an opening on a first surface of the two surfaces and a flap on a second surface of the two surfaces to close or open a flow through the opening.

In one embodiment, the drug chamber contains the at least medication, which is a dry powder medication to treat Asthma and Chronic Obstructive Pulmonary Disease (COPD), and the drug chamber has a size for a measured amount of the dry powder medication for a dose.

In one embodiment, the CID is a cigarette shaped and/or sized, for example 69 mm in length and 24.6 mm in circumference approximately, and convenient device and even available to use in public places without being noticed by surrounding with compliance rate increased and medication reached to most peripheral parts of the lung more effectively.

In one embodiment, the drug chamber contains at least one small tube for a measured amount of the dry powder medication for a dose or seven small tubes for seven days or seven doses.

In one embodiment, the twisted close/open mechanism includes two surfaces with seven openings on each surface for the seven days or the seven doses; and wherein a joint between the two surfaces is marked for a distance to be twisted for each opening of the seven openings. The at least one opening or the seven openings of the each surface of the twisted close/open mechanism have one of a circular, triangle, square or rectangle shape.

In one embodiment, the drug chamber releases medication just prior to inhaling by a patient in a mechanism by twisting at connection with adjacent part or one-way valve to a direction to the patient who start giving suction force.

BRIEF DESCRIPTION OF THE DRAWINGS

Figure 1:
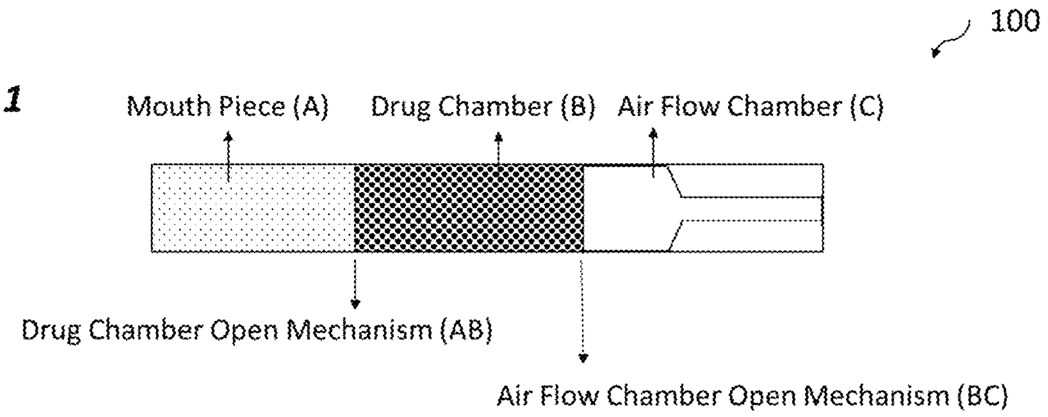

Having thus described embodiments of the invention in general terms, reference will now be made the accompanying drawings, wherein:

FIG. 1 is a general layout of the compact inhalation device including a mouth piece, drug chamber and air flow chamber of the present invention.

Figure 2A:
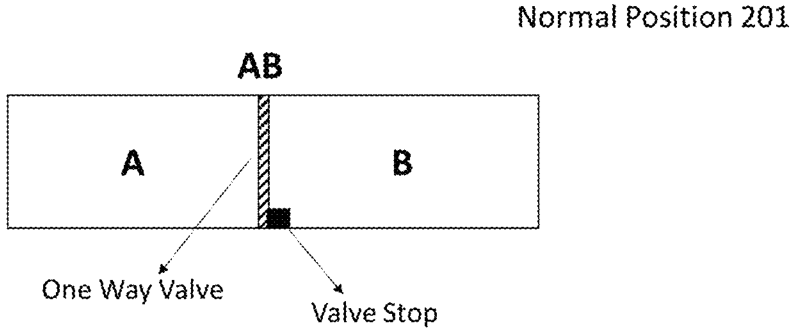
Figure 2B:
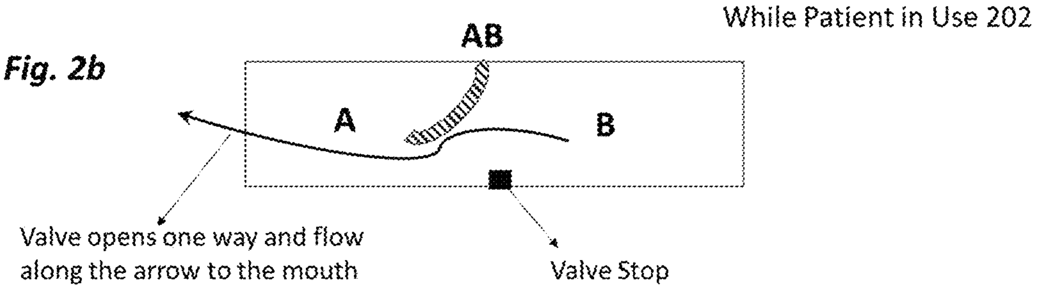

FIGS. 2*a* and 2*b* are component block and air/drug flow diagrams of the device in normal position and while patient in use position.

Figure 3A:
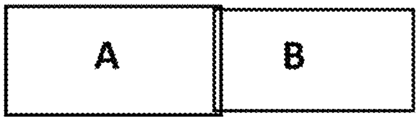
Figure 3B:
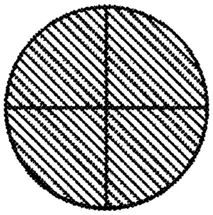
Figure 3C:
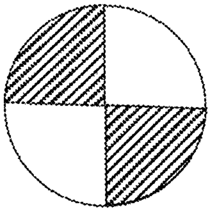

FIGS. 3*a*, 3*b* and 3*c* are layouts of a twisted drug chamber close and open mechanism.

Figure 4A:
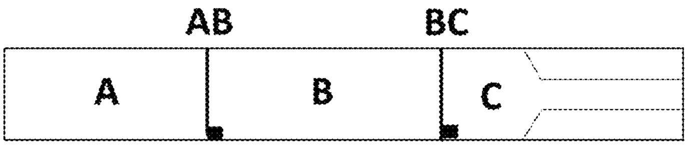
Figure 4B:
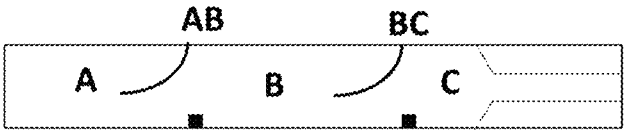

FIGS. 4*a* and 4*b* are layouts of a drug chamber valve and air flow chamber valve using a flapper flow close/open mechanism.

Figure 5A:
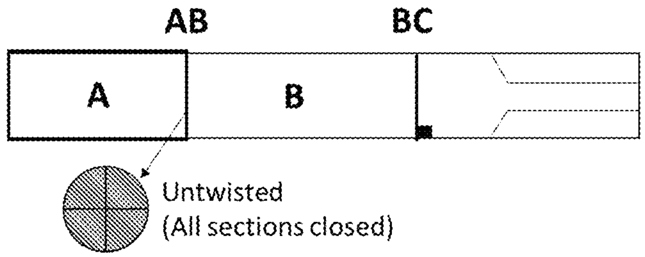
Figure 5B:
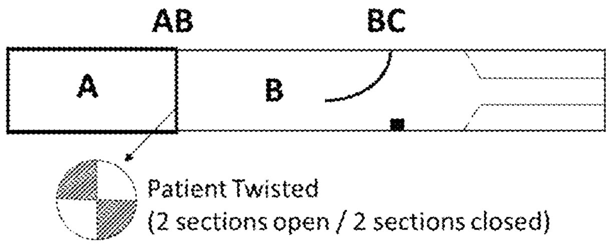
Figure 6A:
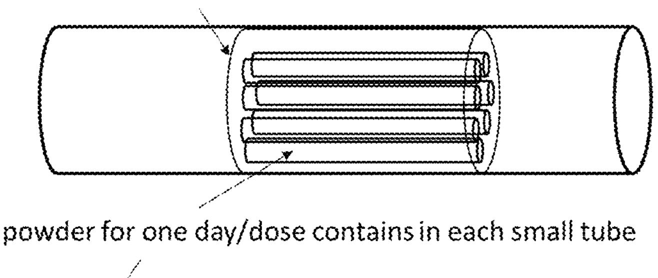
Figure 6B:
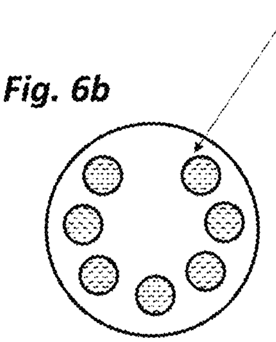
Figure 6C:
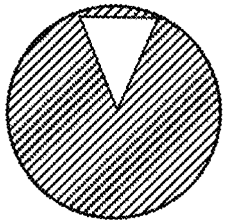
Figure 6D:
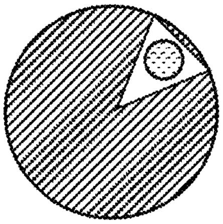

FIGS. 5*a* and 5*b* are combined layouts of a drug chamber valve and air flow chamber valve using a twisted close/open mechanism and a flapper flow close/open mechanism.

FIGS. 6*a*, 6*b*, 6*c* and 6*d* are layouts of a twisted drug chamber with seven mini tubes close and open mechanism.

Figure 7:
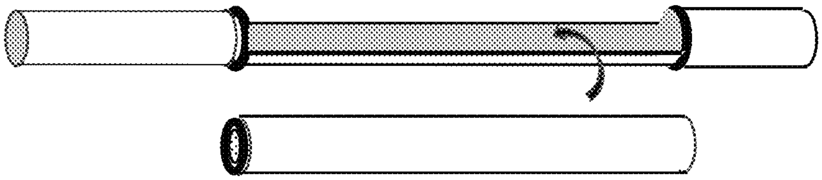

FIG. 7 is a depiction of a medication chamber to insert into a cigarette shaped device.

DETAILED DESCRIPTION OF EMBODIMENTS OF THE INVENTION

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

As will be appreciated by one of skill in the art in view of this disclosure, the present invention may be embodied as a device or method to effectively deliver inhalation medication to a patient. Thus, as described in more detail below, embodiments of the present invention provide for components of the device and specific mechanisms invented to implement the device in the intended purpose.

Turning now to the figures, FIG. 1 illustrates a general layout 100 of the compact inhalation device (CID) including a mouth piece (A), drug chamber (B) and air flow chamber (C), in accordance with embodiments of the present invention. The device is implemented with a drug chamber open/close mechanism (AB) between the mouth piece (A) and the drug chamber (B), as well as an air flow chamber open/close mechanism (BC) between the drug chamber (B) and the air flow chamber (C).

The CID is designed as a tube-shaped device similar to a regular cigarette, for example elongated cylindrical body, made with recycled or reusable materials. The recycled or reusable materials comprise one or combination of paper, meshed paper, meshed reinforced paper, thin plastic, hard rubber, aluminum, thin glass or carbon fiber. The mouth piece, drug chamber and airflow chamber are separable components attachable with an arrangement shown in FIG. 1.

The mouth piece is a part which one end fits by a patient's mouth when use to suck medication and the other end is connected to the medication chamber. The medication (e.g., the drug powder) will flow into the mouth through the mouth piece when the patient start using it. The medication chamber stores measured amount of medication powder to be used. The medication chamber releases medication just prior to inhaling by a user in a mechanism by twisting at connection with adjacent part or one-way valve to a direction to a patient who start giving suction force. The airflow chamber is a top or far end of the CID allowing air from environment to push medication into the patient's mouth through the medication chamber and the mouthpiece.

Referring to FIGS. 2*a* and 2*b*, the figures describe one way valve mechanism for a close and open positions of the joint between the mouth piece and the drug chamber. FIG. 2*a* shows that the one-way valve is in close or normal position 201 when the one-way valve is closed using a valve stop. Moreover, FIG. 2*b* depicts a flap of the one-way valve is in open position to allow the flow of the medication and/or air flow from the drug chamber B to the mouth of the user/patient via the mouth piece A.

FIGS. 3*a*-3*c* depict the twisted close/open mechanism appearing at the joint between the mouth piece and the drug chamber. The mouth piece A and the drug chamber B are coupled with a joint or interfaces providing air tight connection but are capable of being twisted. Each interface of the mouth piece and the drug chamber have an opening, which is aligned each other to provide an opened drug chamber position 303 and is unaligned each other to block a flow of the drug form the drug chamber as in the closed drug chamber position 302.

Referring to FIGS. 4*a* and 4*b*, the CID is implemented the flapped flow close/open mechanism both at the connection or interfaces (AB) between the mouth piece A and the drug chamber B, and at the connection or interfaces (BC) between the drug chamber B and the air flow chamber C. The FIG. 4*a* shows the positions of the one-way valves closing with valve stops for the all valve closed condition and the FIG. 4*b* shows the positions of the flaps of the one-way valves for in use or open condition.

Referring to FIGS. 5*a* and 5*b*, the figures depict mixed or combined use of the twisted close/open mechanism and the flapped flow close/open mechanism in a CID. Either one of the interfaces AB and BC can be implemented with the twisted close/open mechanism or the flapped flow close/open mechanism as a choice of the implementation of the device.

Referring to FIGS. 6*a*-6*d*, the figures show a measured amount of drug in separate tubes for a plurality of doses and open/close mechanisms, which can be implemented to release medication powder of the tubes. The drug chamber contains a small tube for a measured amount of the dry powder medication for a dose, or seven small tubes of the dry powder medication for seven days or seven doses (see FIG. 6*a*). The openings for the seven small tubes can have the twisted close/open mechanism using a circular, triangle, square or rectangle shape of the opening.

Additionally, FIG. 7 illustrates an insertable medication chamber for a different implementation of the CID. The insertable medication chamber can be insert into a slot of a base body, which acts the purpose of the mouth piece and the air flow chamber described above. As an advantage, the insertable medication chamber can be replaced after used and the reusable base body may be made in customized design, shape or material.

Those skilled in the art may appreciate that various adaptations and modifications of the just described embodiments can be configured without departing from the scope and spirit of the invention. Therefore, it is to be understood that, within the scope of the appended claims, the invention may be practiced other than as specifically described herein.

I claim:

1. A compact inhalation device (CID) comprising:

a base body comprising a mouth piece, an air flow chamber, and a drug receiving portion positioned between the mouth piece and the air flow chamber, and a removable drug chamber, wherein the drug receiving portion of the base body comprises a slot configured to receive the removable drug chamber to position the removable drug chamber between the mouth piece and the air flow chamber;

wherein the mouth piece, the drug receiving portion and the air flow chamber are connected to form a cigarette-shaped cylinder; wherein the air flow chamber includes a first end, a second end opposite to the first end of the air flow chamber, and a tapering inner surface that tapers toward an elongated passageway that has an opening forming an inlet; wherein the inlet is positioned on the second end of the air flow chamber that forms a circular face of the cigarette-shaped cylinder; wherein the mouth piece, the drug receiving portion and the air flow chamber are coupled to provide at least one medication contained in the removable drug chamber to a patient via the mouth piece; wherein the at least one medication is a dry powder medication to treat Asthma and Chronic Obstructive Pulmonary Disease (COPD);

wherein one end of the mouth piece is configured to fit the patient's mouth and another end of the mouth piece is connected to a first end of the drug receiving portion using a twisted close/open mechanism; wherein a second end of the drug receiving portion is connected to the first end of the air flow chamber using the flapped flow close/open mechanism, which allows to open by suction force of the patient;

wherein the twisted close/open mechanism includes two surfaces with at least one opening on each surface of the two surfaces of the twisted close/open mechanism wherein aligning the at least one opening of each surface of the two surfaces of the twisted close/open mechanism by twisting provides an open flow condition and unaligned the at least one opening of each surface of the two surfaces of the twisted close/open mechanism to block the at least one opening of each surface of the two surfaces of the twisted close/open mechanism by twisting provides a close flow condition; and wherein the flapped flow close/open mechanism forming a one-way flap valve that includes two surfaces with an opening on a first surface of the two surfaces of the flapped flow close/open mechanism and a flap on a second surface of the two surfaces of the flapped flow close/open mechanism to close or open a flow through the opening of the flapped flow close/open mechanism.

2. The compact inhalation device according to claim 1, wherein the removable drug chamber is a small tube for a measured amount of the dry powder medication of the at least one medication for a dose.

3. The compact inhalation device according to claim 2, wherein a joint between the two surfaces of the twisted close/open mechanism is marked for a distance to be twisted for the at least one opening of the twisted close/open mechanism.

4. The compact inhalation device according to claim 3, wherein the at least one opening of the each surface of the two surfaces of the twisted close/open mechanism have one of a circular shape, triangle shape, square shape or rectangle shape.

5. The compact inhalation device according to claim 1, whereby the removable drug chamber releases the at least one medication: (a) using the twisted close/open mechanism by twisting a portion of the mouth piece, which is adjacent to the drug receiving portion or (b) via the flap of the flapped flow close/open mechanism between the drug receiving portion and the air flow chamber to a direction to the patient who start giving suction force.

6. The compact inhalation device according to claim 5, wherein the one-way flap valve of the compact inhalation device is closed using a valve stop of the air flow chamber while the patient is not giving suction force.

7. The compact inhalation device according to claim 1, wherein the CID is made with recycled or reusable materials, wherein the recycled or reusable materials comprise one or combination of paper, meshed paper, meshed reinforced paper, plastic, rubber, aluminum, glass or carbon fiber.

8. A method for providing a compact inhalation device (CID) to deliver inhalation of at least one medication to a patient, the method comprising:

providing the compact inhalation device comprising a base body, the base body comprising a mouth piece, an air flow chamber, and a drug receiving portion positioned between the mouth piece and the air flow chamber, and a removable drug chamber wherein the drug receiving portion of the base body comprises a slot configured to receive the removable drug chamber to position the removable drug chamber between the mouth piece and the air flow chamber;

coupling the mouth piece, the drug receiving portion and the air flow chamber to form a cigarette-shaped cylinder; wherein the air flow chamber includes a first end, a second end opposite to the first end of the air flow chamber, and a tapering inner surface that tapers toward an elongated passageway that has an opening forming an inlet; wherein the inlet is positioned on the second end of the air flow chamber that forms a circular face of the cigarette-shaped cylinder; wherein the mouth piece, the drug receiving portion and the air flow chamber are coupled to provide at least one medication contained in the removable drug chamber to the patient via the mouth piece; wherein the at least one medication is a dry powder medication to treat Asthma and Chronic Obstructive Pulmonary Disease (COPD);

wherein one end of the mouth piece is configured to fit the patient's mouth and another end of the mouth piece is connected to a first end of the drug receiving portion using a twisted close/open mechanism; wherein a second end of the drug receiving portion is connected to the first end of the air flow chamber using the flapped flow close/open mechanism, which allows to open by suction force of the patient;

wherein the twisted close/open mechanism includes two surfaces with at least one opening on each surface of the two surfaces of the twisted close/open mechanism, wherein aligning the at least one opening of each surface of the two surfaces of the twisted close/open mechanism by twisting provides an open flow condition and unaligned the at least one opening of each surface of the two surfaces of the twisted close/open mechanism to block the at least one opening of each surface of the two surfaces of the twisted close/open mechanism by twisting provides a close flow condition; and wherein the flapped flow close/open mechanism forming a one-way flap valve that includes two surfaces with an opening on a first surface of the two surfaces of the flapped flow close/open mechanism and a flap on a second surface of the two surfaces of the flapped flow close/open mechanism to close or open a flow through the opening of the flapped flow close/open mechanism.

9. The method according to claim 8, wherein the removable drug chamber is a small tube for a measured amount of the dry powder medication of the at least one medication for a dose.

10. The method according to claim 9, wherein a joint between the two surfaces of the twisted close/open mechanism is marked for a distance to be twisted for the at least one opening of the twisted close/open mechanism.

11. The method according to claim 10, wherein the at least one opening of the each surface of the two surfaces of the twisted close/open mechanism have one of a circular shape, triangle shape, square shape or rectangle shape.

12. The method according to claim 8, the method further comprises releasing, by the removable drug chamber, the at least one medication: (a) using the twisted close/open mechanism by twisting a portion of the mouth piece, which is adjacent to the drug receiving portion or (b) via the flap of the flapped flow close/open mechanism between the drug receiving portion and the air flow chamber to a direction to the patient who start giving suction force.

* * * * *